United States Patent [19]

Ono et al.

[11] Patent Number: 5,278,635
[45] Date of Patent: Jan. 11, 1994

[54] SURFACE DEFECT DETECTION APPARATUS

[75] Inventors: Hiroshi Ono; Masahiro Kondo, both of Hachioji, Japan

[73] Assignee: Konica Corporation, Tokyo, Japan

[21] Appl. No.: 961,069

[22] Filed: Oct. 14, 1992

Related U.S. Application Data

[63] Continuation of Ser. No. 672,080, Mar. 19, 1991, abandoned.

[30] Foreign Application Priority Data

Mar. 28, 1990 [JP] Japan ................................. 2-80279
Mar. 29, 1990 [JP] Japan ................................. 2-81920

[51] Int. Cl.⁵ ...................... G01N 21/89; G01N 21/55
[52] U.S. Cl. ..................................... 356/430; 356/429; 356/431; 356/446; 356/237; 356/238; 250/563
[58] Field of Search ............... 356/430, 431, 445, 238, 356/429, 236, 237, 446, 426, 348, 360; 250/223, 572, 563

[56] References Cited

U.S. PATENT DOCUMENTS

3,662,181  5/1972  Hercher et al. ................. 356/223 B
4,671,663  6/1987  Sick ...................................... 356/430

FOREIGN PATENT DOCUMENTS

62-127618  6/1987  Japan .

Primary Examiner—Vincent P. McGraw
Assistant Examiner—LaCharles Keesee
Attorney, Agent, or Firm—Finnegan, Henderson, Farabow, Garrett & Dunner

[57] ABSTRACT

A surface defect detector for detecting a gentle wavy defect and a minute rough defect on a surface of an object. The detector has a conveyer to move the object in a linear direction, a laser beam generator to irradiate a laser beam onto the object in a direction perpendicular to the linear direction, two photoreceptors to generate two different signals in accordance with a reflection of the laser beam from the object, a separator to optically separate the photoreceptors, and a processor to process the signals from the photoreceptors to detect the gentle wavy defect and the minute rough defect.

15 Claims, 9 Drawing Sheets

A-B (a)

(b)

Q    r    Q (d) IMAGE REGION (e) OUTSIDE OF IMAGE REGION

Q    r    Q

SURFACE DEFECT DETECTION APPARATUS

This application is a continuation of application Ser. No. 07/672,080, filed Mar. 19, 1991, now abandoned.

BACKGROUND OF THE INVENTION

The present invention relates to a surface defect detection apparatus for inspecting defects on a surface of a plane or cylindrical matter, and more particularly concerns a surface defect detection apparatus being capable of detecting a rather gentle wavy defect at a high speed.

There has been a known flying spot method to inspect the surface of the plane or cylindrical matter in a non-contact way. In the method, a laser beam is scanned on the moving matter with use of a rotation multi-plane mirror or an oscillation mirror. The light reflected from the matter is different depending on state of the defect. This is used for the inspection.

There are two kinds of defects on the surface of the inspected matter: (1) a wavy defect of relatively gentle roughness and (2) a minute rough defect which causes rough surface. The reflected lights for the wavy defect existing on the surface of the matter and for no defect are shown by a curve n1 of the light reflected from the wavy defect in FIG. 6 and a curve of the light reflected from the good surface in FIG. 5. The center line of the curve of the light reflected from the wavy defect, as seen from the figures, is deviated from the normal reflection direction.

A photo-sensor device can be provided to rightly face the normal reflection direction with the laser beam irradiated to the matter. For the wavy defect, the reflected light will be deviated from the photo-sensor device or made to come in a corner thereof. For the minute rough defect, the laser beam is scattered on the surface of the matter as reflected so that the quantity of the reflected light coming into the photo-sensor-device can be reduced as compared with the normal reflected light (see the curve n2 in FIG. 5).

The two defects (1) and (2) mentioned above may be produced as superimposed on the surface of the matter, or may be independent thereon.

In the inspection of the surface of the matter by the flying spot method, there has been a case that the photo-sensor device can be moved in the scanning direction to receive the light. This, however, takes too much time to do the surface inspection as mechanical movement of the photo-sensor device has to be made.

In contrast to the flying spot method described above, it has been proposed to inspect a surface of a matter in a way that an apparatus has a photo-sensor device having a strip light receiving window fixed for receiving a reflected light of a single scanning and is to move the matter to be inspected. This inspection method allows a whole surface inspection at a high speed.

However, the apparatus can detect the minute rough defect (2) as the quantity of light coming from a defective point is reduced, but is hard to detect the wavy defect (1). The apparatus, therefore, cannot distinguish the wavy defect (1) from the minute rough defect (2).

In view of the foregoing, it is a general object of the present invention to provide a surface defect detection apparatus that can detect the wavy defect (1) at a high speed.

SUMMARY OF THE INVENTION

Briefly, the foregoing object is accomplished in accordance with aspects of a first embodiment and a second embodiment of the present invention. The first embodiment can detect a gentle rough defect on a surface of a matter, characterized in that it has a laser beam scanned and irradiated in a linear way in a direction perpendicular to a direction of movement of the surface of the matter to be inspected; has two rectangular upper and lower photo-sensors divided in a direction of light reflected from the matter by an edge member, the photo-sensors having a diffusion plate provided at a front end thereof; and, signals output of the two photo-sensors are processed by subtraction.

The second embodiment can detect a gentle wavy defect and a minute rough defect of scattering light on a surface of a matter, characterized in that it has a laser beam scanned and irradiated in a linear way in a direction perpendicular to a direction of movement of the surface of the matter to be inspected; has two rectangular upper and lower photo-sensors divided in a direction of light reflected from the matter by an edge member, the photo-sensors having a diffusion plate provided at a front end thereof; and, signals output of the two photo-sensors are processed by subtraction and addition.

DETAILED DESCRIPTION OF THE INVENTION

Figure 1:
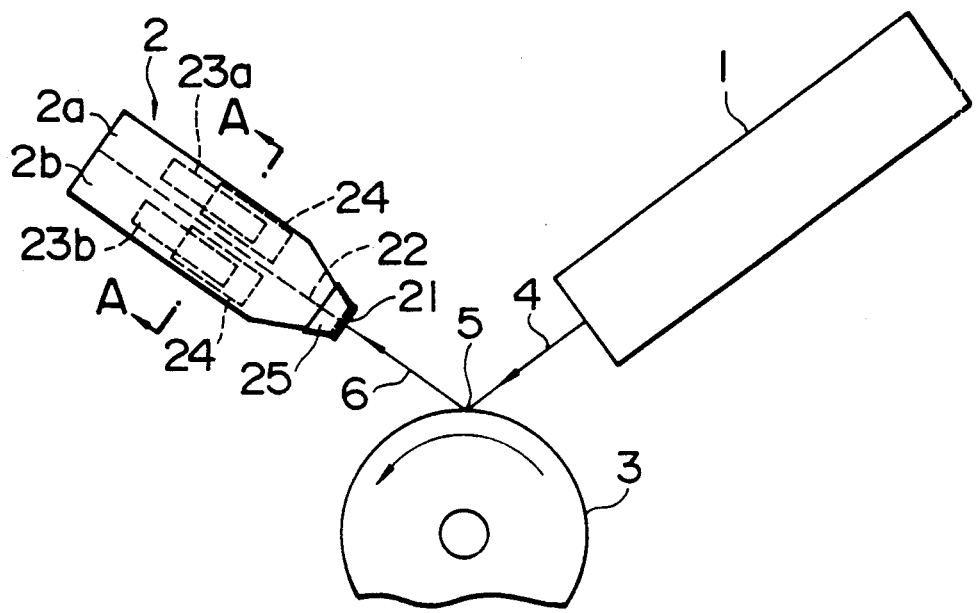
FIG. 1 is a side view showing the embodiment.
Figure 2:
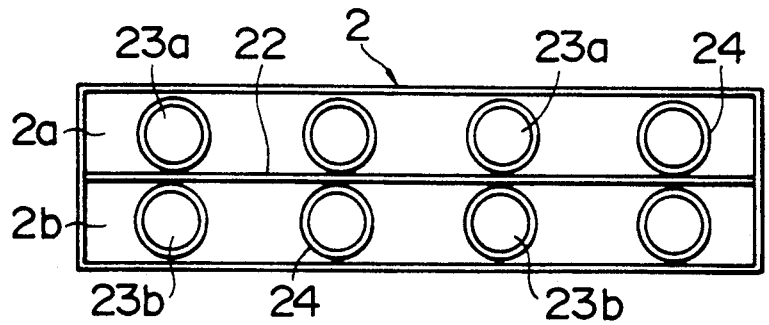
FIG. 2 is a cross sectional view taken by line A—A of a photo-sensor device shown in FIG. 1.
Figure 3:
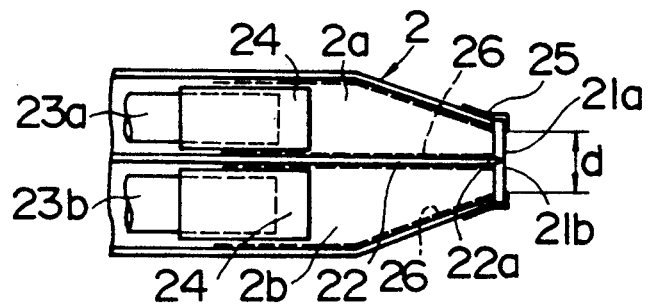
FIG. 3 is a central longitudinal cross sectional view of the photo-sensor device in FIG. 1.
Figure 4:
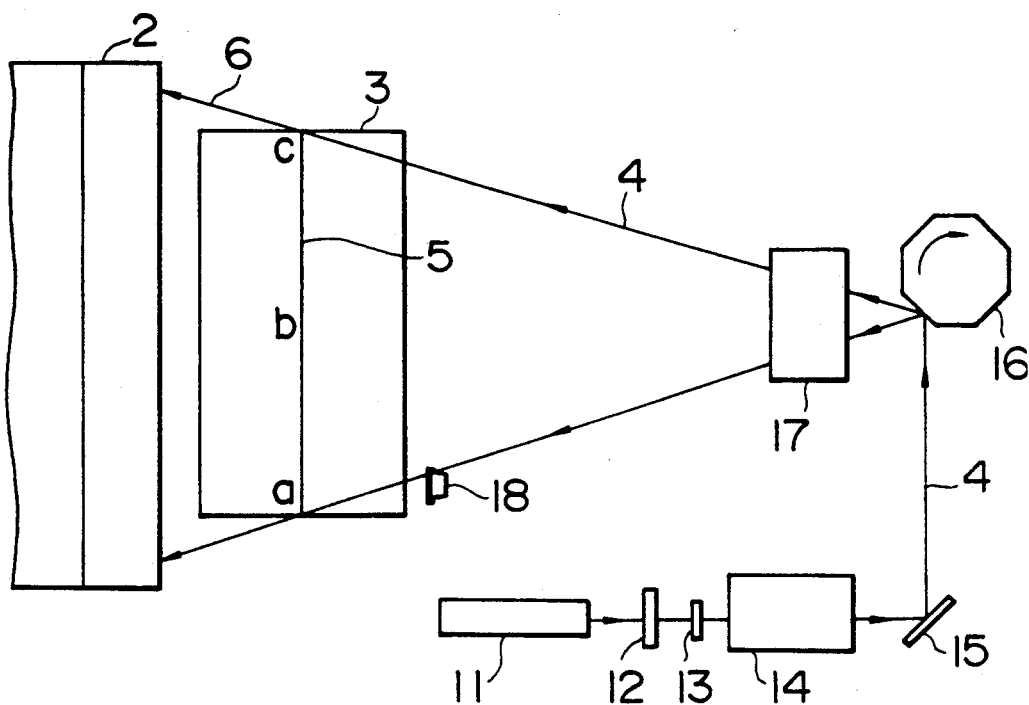
FIG. 4 is an exploded view of a laser beam path in FIG. 1.

The following describes an embodiment of the surface defect detection apparatus according to the present invention with reference to drawings. In the accompanying drawings, FIG. 1 is a side view showing the embodiment. FIG. 2 is a cross sectional view taken by line A—A of a photo-sensor device shown in FIG. 1. FIG. 3 is a central longitudinal cross sectional view of the photo-sensor device in FIG. 1. FIG. 4 is an exploded view of a laser beam path in FIG. 1.

In FIG. 1 are indicated a scanner 1, comprising a laser device, such as a He-Ne laser device, a revolving multi-plane mirror 16, a fθ lens 17, and a synchronous sensor 18; a two photo-sensor device 2, including a photo-sensor A 2a and a photo-sensor B 2b, which are divided by a thin plate or edge member 22 with respect to an incoming light; a light sensitizing drum 3 which is an example of a matter to be inspected; a laser beam 4 which is a scanning light; a scanning bright line 5 drawn on a surface of the matter as the laser beam 4 is scanned and irradiated on it; and, a reflected light 6 from the surface of the matter.

FIG. 4 shows structure and an example of exploded laser beam path of the scanner 1. Preferably, the laser beam 4 is a generated He-Ne laser 11. It is passed through a shutter 12 which is made open as necessary and a ½ wavelength plate 13, as an example, and is magnified to an adequate beam diameter by a beam magnifier 14. The laser light 4 is scanned by the revolving multi-plane mirror 16 and the fθ lens 17 to form the scanning bright line 5 on the surface of the light sensitizing drum 3 to be inspected at an equal speed in parallel with its rotation axis in a direction of a to c through b in the figure. The light sensitizing drum 3, on the other hand, can be revolved at an equal speed in a direction of an arrow to be scanned and irradiated on the whole surface by the laser light 4 as controlled by a controller CPU. The reflected light 6 is received by the photo-sensor 2. The synchronous sensor 18 comprising photo-sensors having a sensitivity for the laser light 4 can send a synchronizing signal to the controller CPU at the start of scanning every time the scanner 1 makes scanning.

The photo-sensor device 2 is divided to an upper and lower sections by the edge member 22 as shown in FIGS. 2 and 3. The divided photo-sensor A 2a and photo-sensor B 2b have pluralities of (for example, four) photo multipliers A 23a and photo multipliers B 23b provided at equal intervals therein, respectively. Each photo multiplier has a cylindrical magnetic shielding member 24 of magnetic substance enclosed thereon at its end. The photo-sensor device 2 has diffusion plates 21a and 21b and a masking member 25 provided at a light receiving window of an end thereof. The masking member 25 can limit a light reception width to d. An end portion 22a of the edge member 22 is formed sharp. If a thin plate of around 0.2 mm thick is used for the edge member 22, it may not be formed sharp. The photo-sensor A 2a and photo-sensor B 2b have a reflecting layer 26 made of specular member or white diffusion member provided on inside walls thereof. These parts are arranged so that the reflected light 6 can be made to come into the diffusion plates 21a and 21b to diffuse, and be reflected by the inside walls until the light can be effectively received by the photo multipliers A 23a and photo multipliers B 23b. In a case that the diffusion plates 21a and 21b are not provided, high inspection accuracy cannot be obtained unless the scanner 1, the photo-sensor device 2, and light sensitizing drum 3 are adjusted precisely and strictly in their relative positions, and inclination of the photo-sensor device 2 to the reflected light 6 also must be adjusted precisely and strictly With the diffusion plates 21a and 21b provided, little deviations of the positions and inclination will not affect the inspection accuracy although this is lowered slightly.

Figure 5:
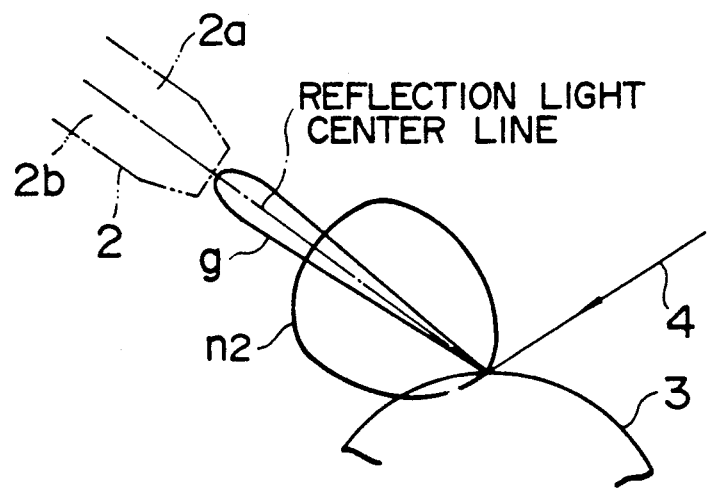
FIG. 5 shows in polar coordinates distribution curves of the reflected light for a good state and a bad state having minute defects on the surface of the inspected matter.
Figure 7:
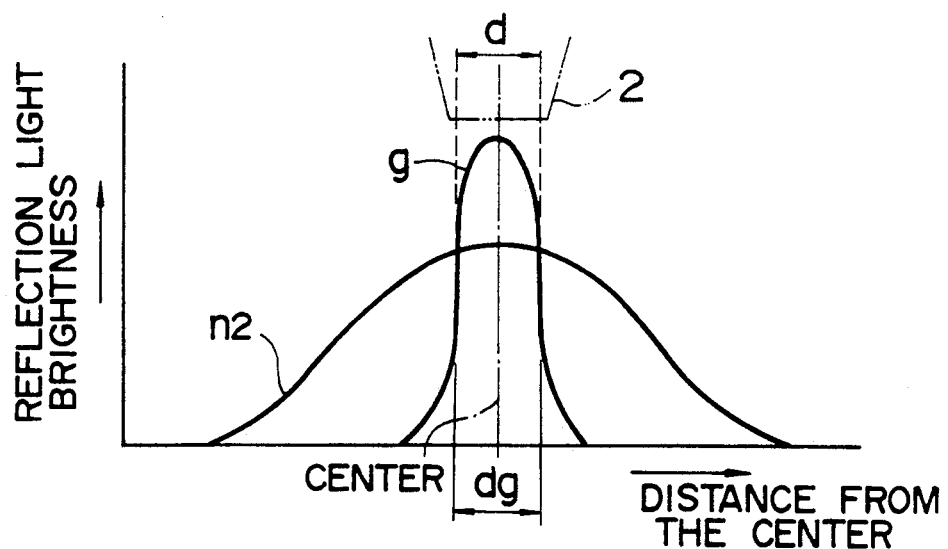
FIG. 7 shows the distributions of the reflected light at a position of the light receiving window of the photo-sensor device.

In turn, operation of the photo-sensor device 2 of the present invention is described below. FIG. 5 shows in polar coordinates, distribution curves of the reflected light for a good state and a bad state having minute defects on the surface of the inspected matter. FIG. 7 shows the distributions of the reflected light at a position of the light receiving window of the photo-sensor device 2. In FIG. 5, a curve g indicates the distribution of the reflected light for the good state of the surface, and n2 is that of the bad state having unevenness. The reflected light 6 given in FIG. 1 is normally distributed in FIG. 7. The width d of the light incoming window limited by the masking member 25 is determined in connection to a masking width dg which is a point of intersection of the curve g shown in FIG. 7 with a curve n2 having the minute defect and possible eccentricity (for cylindrical shape) or deviation (for sheet-like shape) of the inspected matter though it depends on size of the defect to be inspected for the best sensitivity. A good result was obtained, for example, when a diameter of bright spot of the laser beam 4 was 55 μmm on the scanned surface, and the width d is 20 mm.

Figure 6:
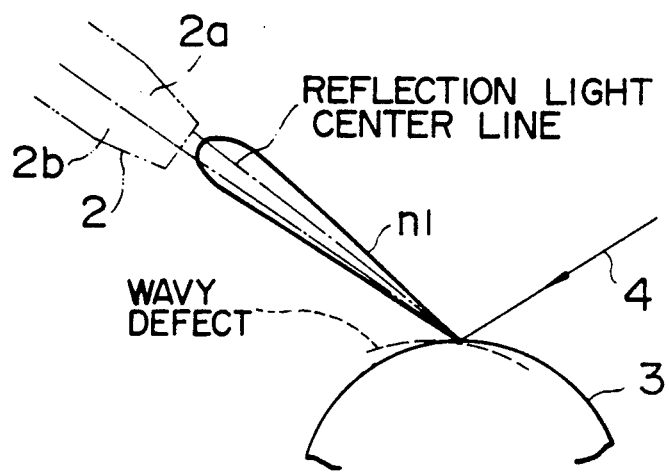
FIG. 6 shows in polar coordinates a distribution curve of the reflected light for a state having a wavy defect on the surface of the inspected matter.

FIG. 6 shows in polar coordinates a distribution curve n1 of the reflected light for a state having a wavy defect on the surface of the inspected matter. For the wavy defect, as shown in the figure, a center line of the reflected light distribution curve is slanted only, but quantity of the reflected light is not changed substantially. A conventional photo-sensor comprising a single light receiving section having a rather larger light receiving window could not detect such a defect the quantity of the received light will not virtually change.

However, with use of the photo-sensor device 2 having the two photo-sensor sections, the photo-sensor A 2a and the photo-sensor B 2b, in the present invention, as shown in FIG. 6, the photo-sensor A 2a and the photo-sensor B 2b can differentiate quantities of the received lights. As a result, the photo multipliers A 23a and the photo multipliers B 23b are different in the output signals. A difference of the two output signals can be used as detection of the wavy defect.

Figure 8:
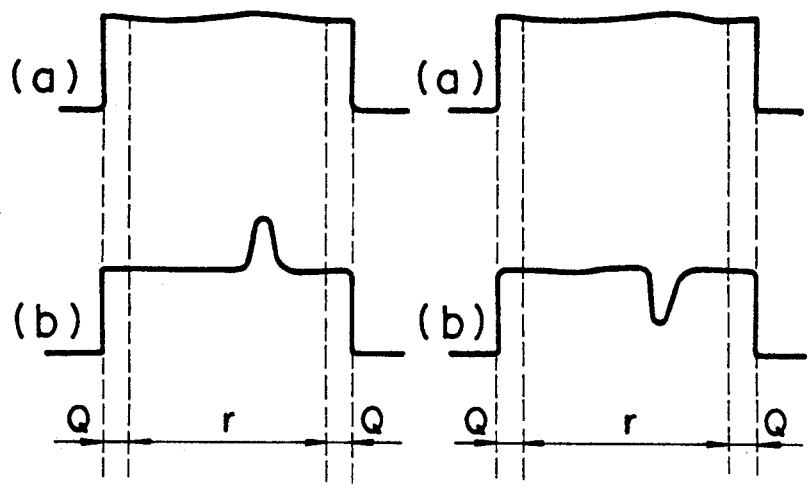
FIG. 8 shows an output signal of the photo-sensor A, and an output signal of the photo-sensor B, obtained by a single scanning of the laser beam according to the present invention, and expressing the photoelectronic output for presence and absence of the wavy defect on the surface of the light sensitizing drum.

FIG. 8 shows an output signal of the photo-sensor A 2a, or the output signal of the photo multiplier A 23a, and an output signal of the photo-sensor B 2b, or the output signal of the photo multiplier B 23b, obtained by a single scanning of the laser beam 4 for presence and absence of the wavy defect on the surface of the light sensitizing drum 3. In the figure, the left hand side curves are of the output signal of the photo-sensor A 2a, and the right hand side curves are of the output signal of the photo-sensor B 2b. Curves (a) are for the good surface, curves (b) for the bad surface having large wavy defect in the vicinity of a center thereof. In the figure are indicated image regions r of the surface of the light sensitizing drum 3 and non-image regions q on both sides of the light sensitizing drum 3.

Figure 9:
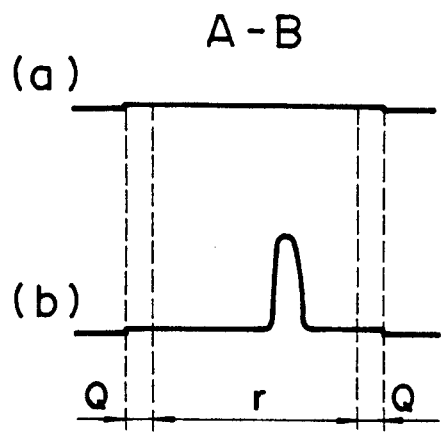
FIG. 9 shows differences of the output curves in FIG. 8.

Differences A-B of the output curves in FIG. 8 are shown in FIG. 9. As a result, the difference of the output signal of the photo-sensor A 2a and the output signal of the photo-sensor B 2b can be used as detection of the wavy defect.

Figure 10:
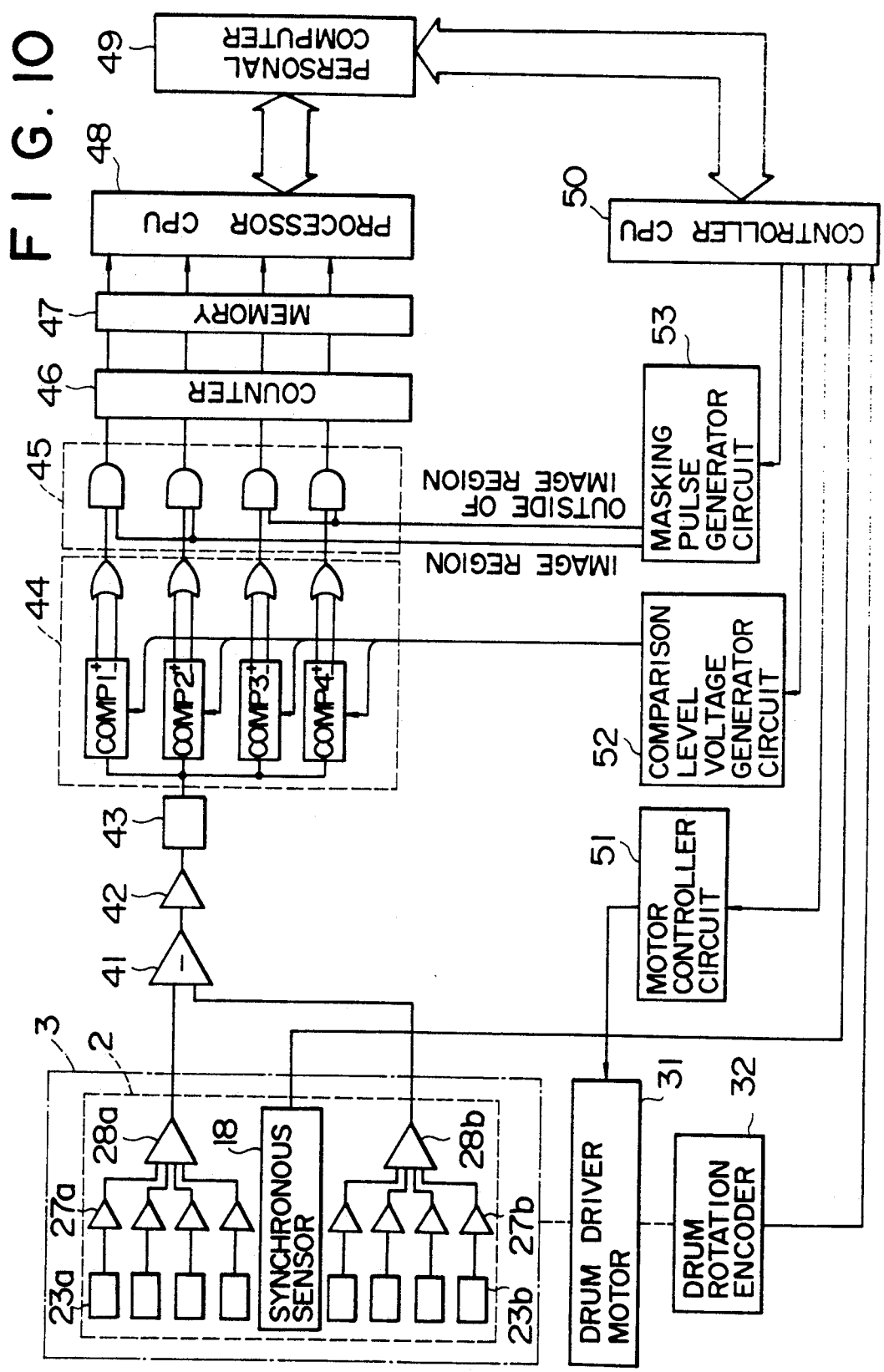
FIG. 10 is a block diagram for an electronic circuit of a first embodiment of the present invention wherein the defect mentioned above can be detected from the outputs of the photo-sensor device.
Figure 12:
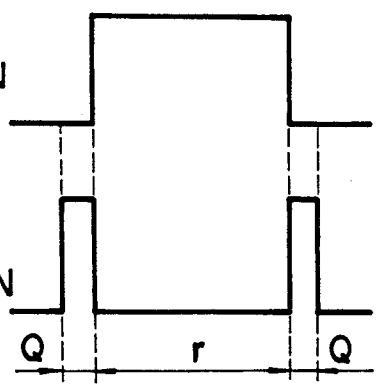
FIG. 12 shows a masking pulse waveform.

FIG. 10 is a block diagram for an electronic circuit of a first embodiment of the present invention wherein the defect mentioned above can be detected from the outputs of the photo-sensor section 2. The controller CPU 50 connected to a personal computer 49 has drum rotation angle information fed out of a drum rotation encoder 32 directly connected to the light sensitizing drum 3 to be inspected. It also has a laser beam scanning start point signal input from the synchronous sensor 18. With the inputs, the controller CPU 50 can drive a drum driver motor 31 through a motor controller circuit 51 to rotate the light sensitizing drum 3 at a predetermined equal rotation speed. A masking pulse generator circuit 53 can feed to a gate section 45 an image region masking pulse (d) and an outside image region masking pulse (e) shown in FIG. 12. A comparison level voltage generator circuit 52 can feed to a comparator section 44 comparison level voltages.

Figure 11:
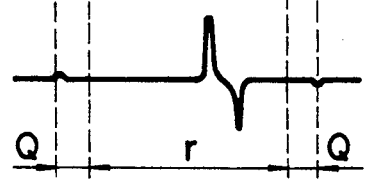
FIG. 11 shows the differentiated waveform which has pulse-like rising and falling portions at the defective point.

The signals output of the four photo multiplier A 23a in the photo-sensor A 2a are through preamplifiers 27a, and are summed up by an addition amplifier 28a. Similarly, the signals output of the four photo multiplier B 23b in the photo-sensor B 2b are through preamplifiers 27b, and are summed up by an addition amplifier 28b. The added signals output of the photo-sensor A 2a and the photo-sensor B 2b are subtracted by a substractor 41 and differentiated by a differentiating circuit 42. The differentiated waveform is shown in FIG. 11, which has pulse-like rising and falling portions at the defective point. The output signal is made to become further clear pulse waveform through a band pass filter 43, and is fed to the comparator section 44.

The comparator section 44 can compare the output pulse with a plurality of comparison level voltages fed by the comparison level voltage generator circuit 52. The plurality of (for example, four) comparators can feed pulse signals through the gate section 45 to a counter section 46 when the output signal exceeds the respective comparison level voltages. The gate section 45 has a plurality of AND circuits therein. The AND circuits allow passing of only the pulse which has come inside the masking pulses (d) and (e) shown in FIG. 12, which are fed from the masking pulse generator circuit 53. The passed pulse is then fed to the counter section 46 having four group counters provided for the inside and outside of the image region.

In the process described above, the pulses are classified with respect to the inside and outside of the image region and large and small sizes of the defects, and are stored in a memory 47. The stored information is processed by a processor CPU 48. The personal computer 49 then displays inspection results of the light sensitizing drum 3 and other control data.

So far, the first embodiment classifies the inspection data of the wavy defect into the four groups, the inside and outside of the image region and the large or small sizes of the defects. The present invention should not be limited to it, but as a matter of course the number of the groups can be increased as necessary.

In accordance with the first embodiment of the present invention, the surface defect detection apparatus provided in the construction, control, and process described above can detect rather gentle wavy defects that could not be detected conventionally.

Figure 13:
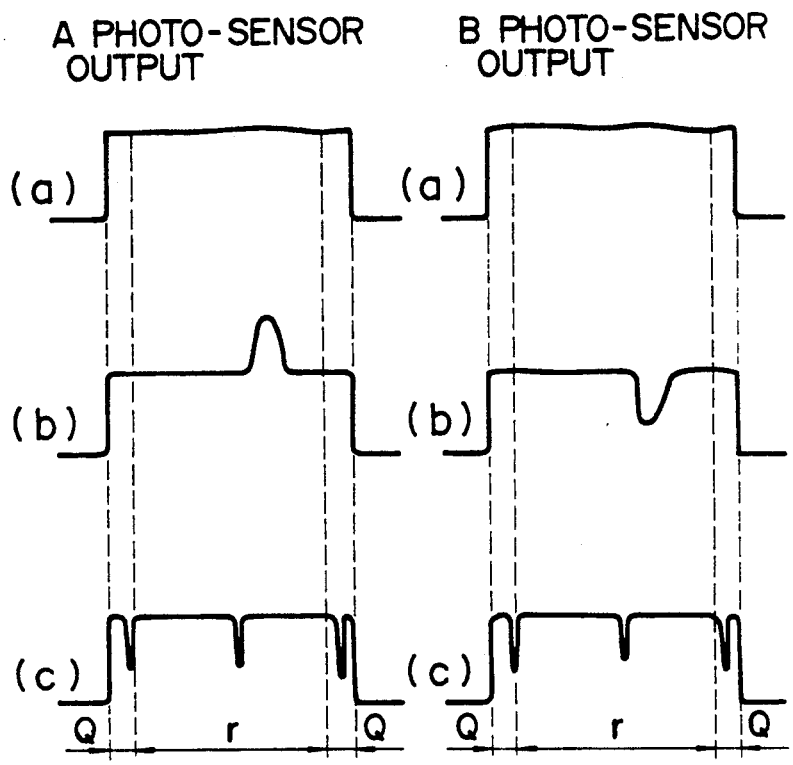
FIG. 13 shows an output signal of the photo-sensor A and an output signal of the photo-sensor B obtained by a single scanning of the laser beam for presence of the wavy defect and minute rough defect on the surface of the light sensitizing drum.

Also in accordance with the present invention, it is possible to provide a second embodiment which can detect even minute rough defects. FIG. 13 shows an output signal of the photo-sensor A 2a, or the output signal of the photo multiplier A 23a, and an output signal of the photo-sensor B 2b, or the output signal of the photo multiplier B 23b, obtained by a single scanning of the laser beam 4 for presence of the wavy defect and minute rough defect on the surface of the light sensitizing drum 3. In the figure, the left hand side curves are of the output signal of the photo-sensor A 2a, and the right hand side curves are of the output signal of the photo-sensor B 2b. Curves (a) are for the good surface, curves (b) are for the bad surface having large wavy defect in the vicinity of a center thereof, and (c) are for the bad surface having the minute defects at the center of the inside of the image region and in the both outsides of the image region. In the figure are indicated image regions r of the surface of the light sensitizing drum 3 and non-image regions q on both sides of the light sensitizing drum 3.

Figure 14:
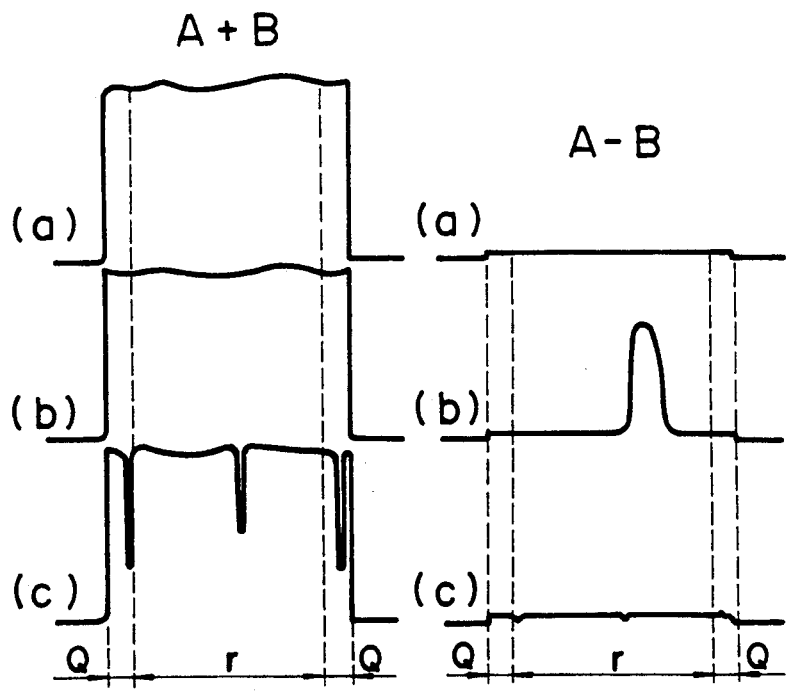
FIG. 14 shows sums and differences of the output curves in FIG. 13.

Sums A+B and differences A−B of the output curves in FIG. 13 are shown at the left hand and right hand in FIG. 14, respectively. As a result, the sum of the output signal of the photo-sensor A 2a and the output signal of the photo-sensor B 2b can be used as detection of the minute rough defect. The difference of the output signal of the photo-sensor A 2a and the output signal of the photo-sensor B 2b can be used as detection of the wavy defect.

Figure 15:
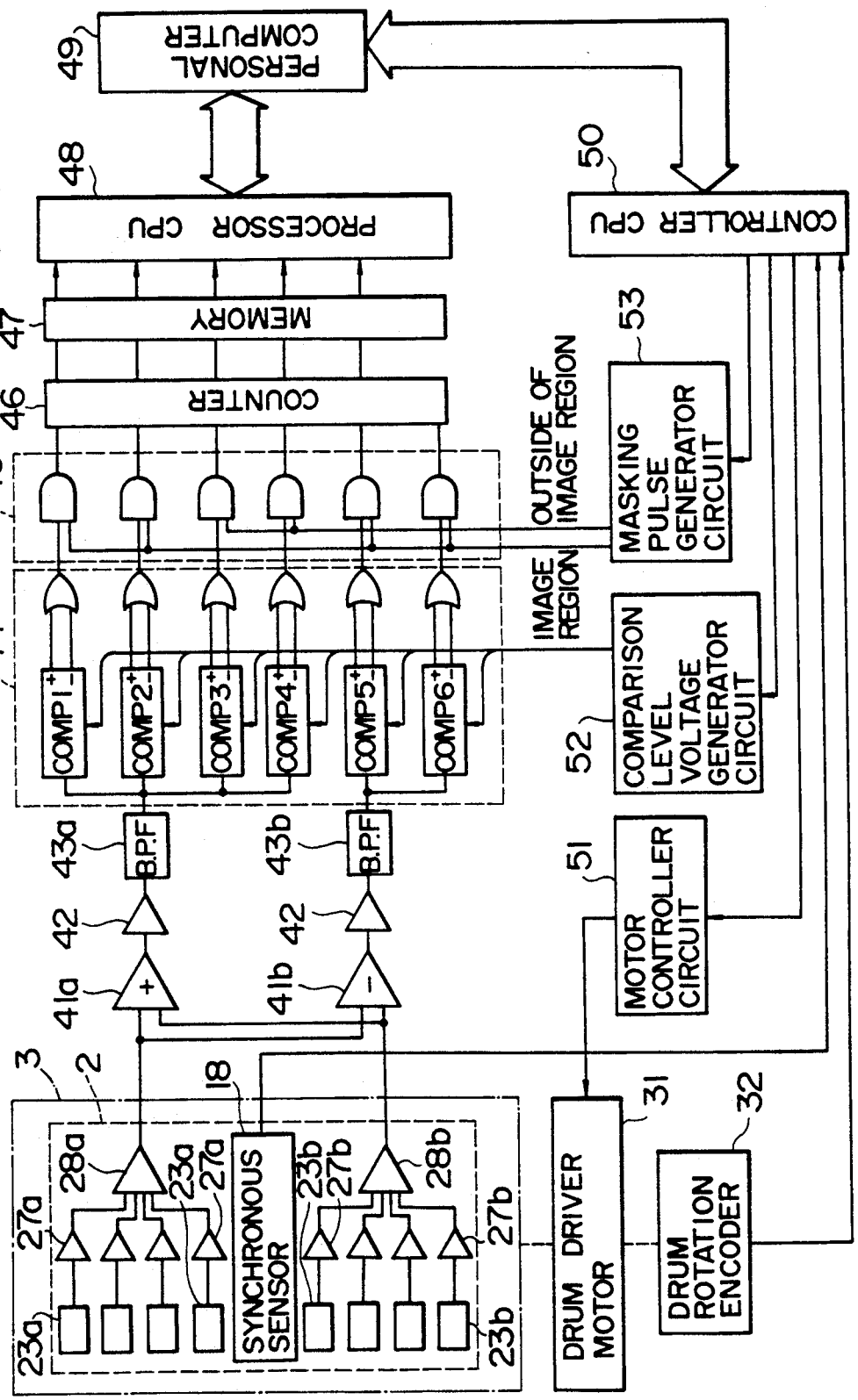
FIG. 15 is a block diagram for an electronic circuit of a second embodiment of the present invention wherein the defect mentioned above can be detected from the outputs of the photo-sensor device.
Figure 17:
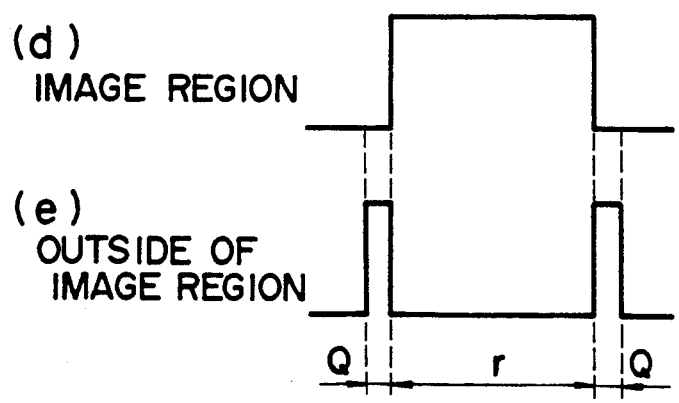
FIG. 17 shows a masking pulse waveform.

FIG. 15 is a block diagram for an electronic circuit of a second embodiment of the present invention wherein the defect mentioned above can be detected from the outputs of the photo-sensor device 2. The controller CPU 50 connected to a personal computer 49 has drum rotation angle information fed out of a drum rotation encoder 32 directly connected to the light sensitizing drum 3 to be inspected. It also has a laser beam scanning start point signal input from the synchronous sensor 18. With the inputs, the controller CPU 50 can drive a drum driver motor 31 through a motor controller circuit 51 to rotate the light sensitizing drum 3 at a predetermined equal rotation speed. A masking pulse generator circuit 53 can feed to a gate section 45 an image region masking pulse (d) and an outside image region masking pulse (e) shown in FIG. 17. A comparison level voltage generator circuit 52 can feed to a comparator section 44 comparison level voltages.

The signals output of the four photo multiplier A 23a in the photo-sensor A 2a are magnified through preamplifiers 27a, and are summed up by an addition amplifier 28a. Similarly, the signals output of the four photo multiplier B 23b in the photo-sensor B 2b are magnified through preamplifiers 27b, and are summed up by an addition amplifier 28b. The added signals output of the photo-sensor A 2a and the photo-sensor B 2b are added by an adder 41a and differentiated by a differentiating circuit 42a. The differentiated waveform is shown at the left hand side in FIG. 16, which has pulse-like rising and falling portions at the minute rough defective point. The added signals output of the photo-sensor A 2a and the photo-sensor B 2b are subtracted by a substractor 41b and differentiated by a differentiating circuit 42b.

Figure 16:
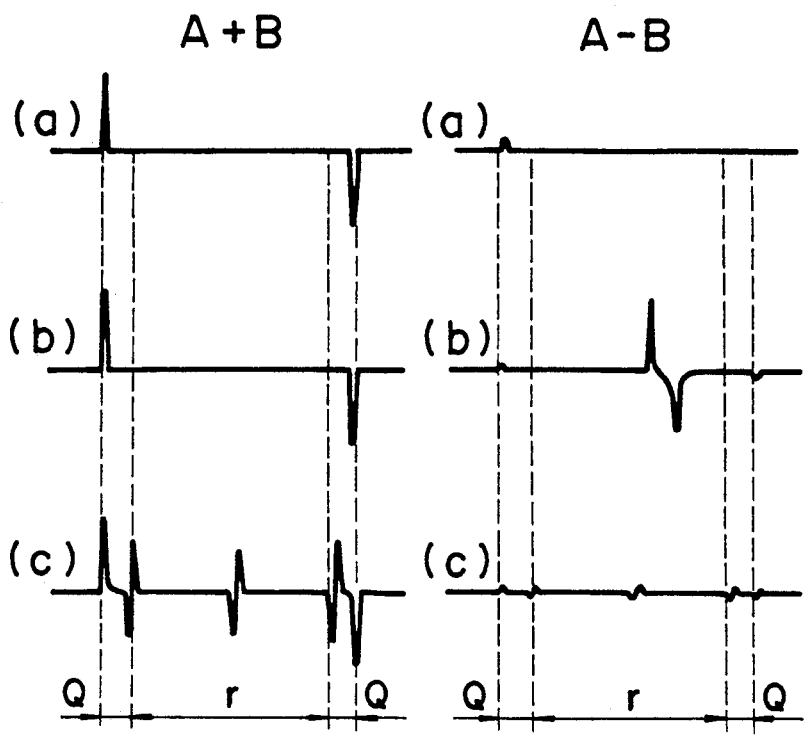
FIG. 16 shows a waveform to which the waveform in FIG. 14 is differentiated.

The differentiated waveform is shown at the right hand side in FIG. 16, which has pulse-like rising and falling portions at the defective point.

The output signals are made to become further clear pulse waveforms through band pass filters 43a and 43b, and are fed to the comparator section 44. It should be noted that a pass band of the band pass filter 43b is slightly lower than that of the band pass filter 43a.

The comparator section 44 can compare the output pulse with a plurality of comparison level voltages fed by the comparison level voltage generator circuit 52. The plurality of (for example, six) comparators can feed pulse signals through the gate section 45 to a counter section 46 when the output signal exceeds the respective comparison level voltages. The gate section 45 has a plurality of AND circuits therein. The AND circuits allow passing of only the pulse can come inside the masking pulses (d) and (e) shown in FIG. 17, which are fed from the masking pulse generator circuit 53. The passed pulse is then fed to the counter section 46 having six group counters provided for the inside and outside of the image region.

In the process described above, the pulses are classified with respect to the inside and outside of the image region, kind of defect, and large and small sizes of the defects, and are stored in a memory 47 having six group memories. The stored information is processed by a processor CPU 48. The personal computer 49 then displays inspection results of the light sensitizing drum 3 and other control data.

So far, the second embodiment classifies the inspection data of the six groups, the four groups for the minute rough defects inside and outside the image region and the large and small sizes and the two groups for the wavy defects inside the image region. The present invention should not be limited to it, but as a matter of course the number of the groups can be increased as necessary.

In accordance with the second embodiment of the present invention, the surface defect detection apparatus provided in the construction, control, and process described above can detect rather gentle wavy defects that could not be detected conventionally. It also can detect the minute rough defects that could not be detected conventionally.

What is claimed is:

1. An apparatus for detecting a gentle wavy defect on a surface of an object, comprising:
   means for conveying said object in a first direction;
   means for irradiating a laser beam onto said object in a direction perpendicular to said first direction, wherein said irradiating means includes means for scanning said laser beam in said direction perpendicular to said first direction;
   first means for generating a first signal in accordance with a direct refection of said laser beam from said object;
   second means for generating a second signal in accordance with said direct reflection of said laser beam from said object;
   means for optically separating said first generating means from said second generating means so that said first generating means and said second generating means receive said direct reflection of said laser beam independently;
   a diffuser for diffusing said direct reflection of said laser beam, said diffuser being positioned so that said direct reflection of said laser beam is independently received by said first generating means and said second generating means through said diffuser; and
   means for processing said first signal and said second signal so that said gentle wavy defect is detected.

2. The apparatus of claim 1, wherein said processing means includes means for subtracting said first signal from said second signal for detecting said way defect.

3. An apparatus for detecting a gentle wavy defect and a minute rough defect on a surface of an object, comprising:
   means for conveying said object in a first direction;
   means for irradiating a laser beam onto said object in a direction perpendicular to said first direction, wherein said irradiating means includes means for scanning said laser beam in said direction perpendicular to said first direction;
   first means for generating a first signal in accordance with a direct reflection of said laser beam from said object;
   second means for generating a second signal in accordance with said direct reflection of said laser beam from said object;
   means for optically separating said first generating means from said second generating means so that said first generating means and said second generating means receive said direct reflection of said laser beam independently;
   a diffuser for diffusing said direct reflection of said laser beam, said diffuser being positioned so that said direct reflection of said laser beam is independently received by said first generating means and said second generating means through said diffuser; and
   means for processing said first signal and said second signal so that said gentle wavy defect and said minute rough defect are detected.

4. The apparatus of claim 1, wherein said separating means includes a panel-like edge member positioned between said first generating means and said second generating means.

5. The apparatus of claim 6, wherein the edge member of said separating means has a forward end directed toward said object, the forward end having a thickness of no more than about 0.2 mm.

6. The apparatus of claim 1, wherein said processing means includes means for classifying characteristics of said gentle wavy defect, and means for storing the classified characteristics.

7. The apparatus of claim 3, wherein said processing means includes means for subtracting said first signal from said second signal for detecting said gentle wavy defect and adding said first signal to said second signal for detecting said minute rough defect.

8. The apparatus of claim 6, wherein said classifying means includes means for determining an image region location and a size of said gentle way defect.

9. The apparatus of claim 3, wherein said processing means further includes means for classifying characteristics of said gentle wavy defect and of said minute rough defect, and means for storing the classified characteristics.

10. The apparatus of claim 3, wherein said separating means includes a panel-like edge member positioned between said first generating means and said second generating means.

11. An apparatus for detecting a defect on a surface of an object, comprising:

means for conveying said object in a first direction;

means for irradiating a laser beam onto said object in a direction perpendicular to said first direction, wherein said irradiating means includes means for scanning said laser beam in said direction perpendicular to said first direction;

first means for generating a first signal in accordance with a direct reflection of said laser beam from said object;

second means for generating a second signal in accordance with said direct reflection of said laser beam from said object;

mean for optically separating said first generating means from said second generating means so that said first generating means and said second generating means receive said direct reflection of said laser beam independently; and means for processing said first signal and said second signal so that said defect is detected, said processing means includes means for identifying whether said defect is a gently wavy type defect or a minute rough type defect.

12. The apparatus of claim 1, wherein said processing means includes means for subtracting said first signal from said second signal for identifying said gentle wavy type defect and for adding said first signal to said second signal for identifying said minute rough type defect.

13. The apparatus of claim 12, wherein said processing means further includes means for classifying characteristics of said defect, and means for storing the classified characteristics.

14. The apparatus of claim 11, wherein said separating means includes a panel-like edge member positioned between said first generating means and said second generating means, the edge member having a forward end directed toward said object, the forward end having a thickness of no more than about 0.2 mm.

15. The apparatus of claim 14 further comprising a diffuser for diffusing said direct reflection of said laser beam, said diffuser being positioned proximate the forward end of the edge member so that said direct reflection of said laser beam is independently received by said first generating means and said second generating means through said diffuser.

* * * * *